(12) United States Patent
Diao

(10) Patent No.: US 10,136,931 B1
(45) Date of Patent: Nov. 27, 2018

(54) BONE FIXATION DEVICE AND METHOD

(71) Applicant: Edward Diao, San Francisco, CA (US)

(72) Inventor: Edward Diao, San Francisco, CA (US)

( * ) Notice: Subject to any disclaimer, the term of this patent is extended or adjusted under 35 U.S.C. 154(b) by 210 days.

(21) Appl. No.: 15/386,452

(22) Filed: Dec. 21, 2016

Related U.S. Application Data

(60) Provisional application No. 62/270,229, filed on Dec. 21, 2015.

(51) Int. Cl.
*A61B 17/80* (2006.01)
*A61B 17/56* (2006.01)
*A61B 17/68* (2006.01)

(52) U.S. Cl.
CPC .......... *A61B 17/8004* (2013.01); *A61B 17/56* (2013.01); *A61B 17/80* (2013.01); *A61B 17/808* (2013.01); *A61B 17/8009* (2013.01); *A61B 17/8014* (2013.01); *A61B 17/8019* (2013.01); *A61B 2017/564* (2013.01); *A61B 2017/681* (2013.01)

(58) Field of Classification Search
CPC .............. A61B 17/56; A61B 2017/564; A61B 2017/681; A61B 17/80; A61B 17/8004; A61B 17/8009; A61B 17/8014; A61B 17/8019; A61B 17/808
See application file for complete search history.

(56) References Cited

U.S. PATENT DOCUMENTS

| | | | | |
|---|---|---|---|---|
| 7,635,365 B2* | 12/2009 | Ellis | .................... | A61B 17/8076 606/71 |
| 8,177,819 B2* | 5/2012 | Huebner | ................ | A61B 17/80 606/281 |
| 8,784,458 B1* | 7/2014 | White | .................... | A61B 17/80 606/288 |
| 9,339,313 B1* | 5/2016 | Powlan | ................ | A61B 17/746 |
| 9,775,657 B2* | 10/2017 | Bernstein | ............. | A61B 17/808 |
| 2013/0261674 A1* | 10/2013 | Fritzinger | ............ | A61B 17/808 606/286 |
| 2016/0095636 A1* | 4/2016 | Wiederkehr | ....... | A61B 17/8033 606/281 |

* cited by examiner

*Primary Examiner* — Larry E Waggle, Jr.
(74) *Attorney, Agent, or Firm* — Staniford Tomita LLP

(57) ABSTRACT

A bone fixation device includes an elongated bone fixation plate and a rotational member that are secured to an oblique fractured bone. The fixation plate can be secured to the bone across the fracture. The rotation member can include two tabs that extend around opposite sides of the bone. The bone segments can be aligned and secured to the fixation plate. The rotation member can then be rotated so that the tabs physically contact and prevent movement of the bone segments.

18 Claims, 7 Drawing Sheets

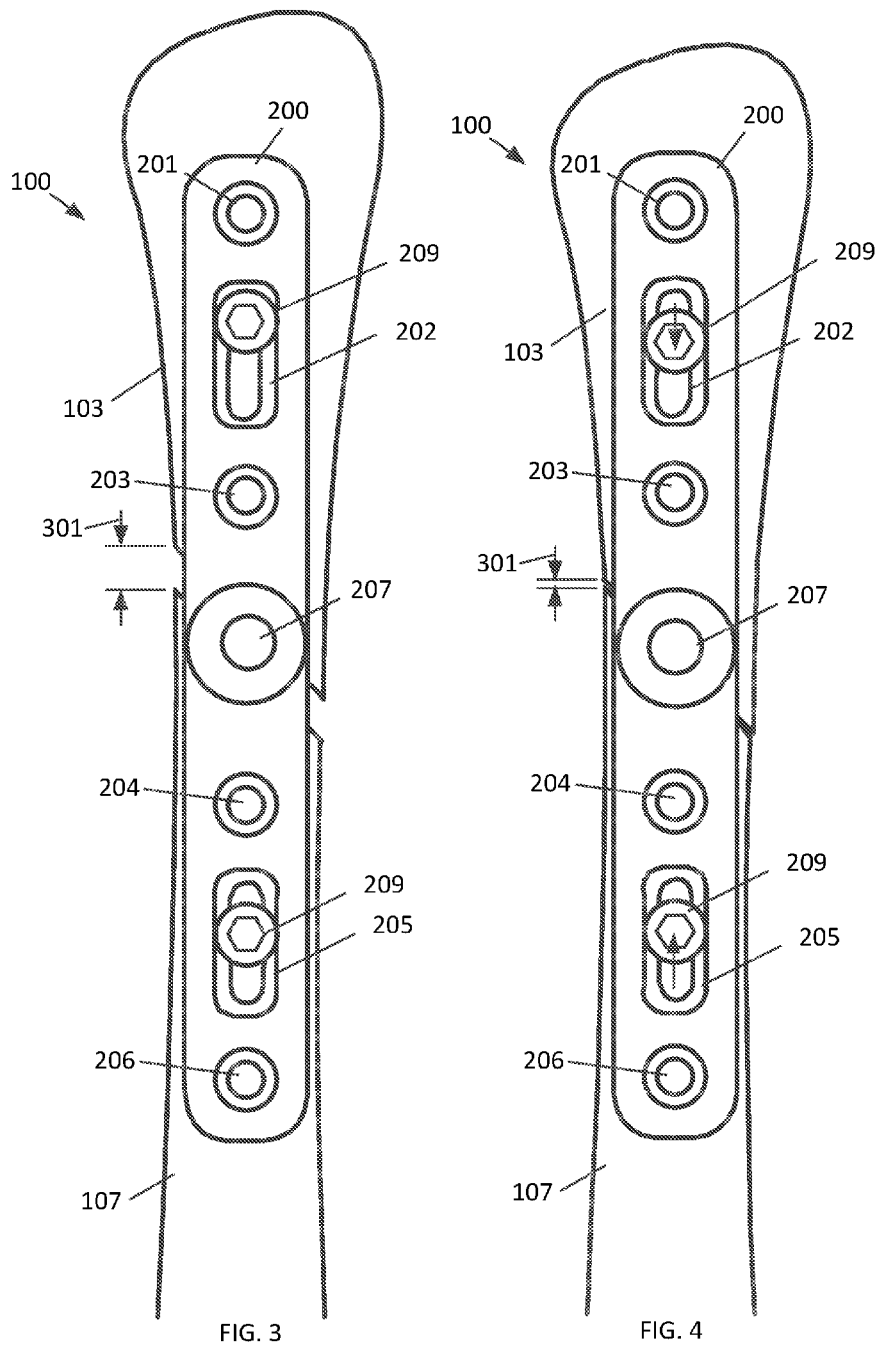

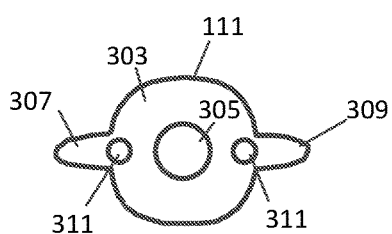
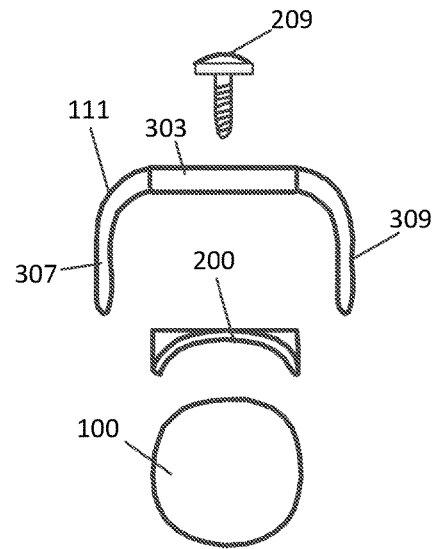
FIG. 5
FIG. 6
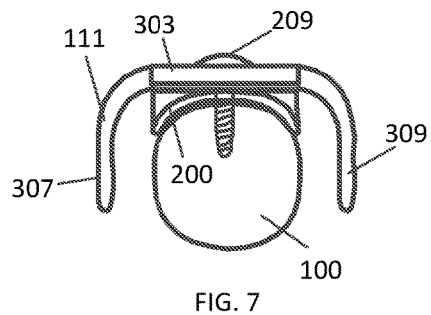
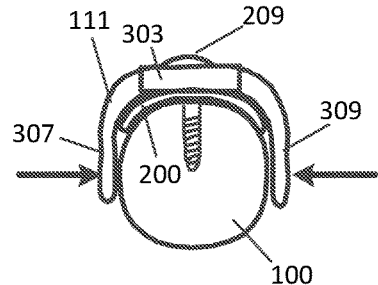
FIG. 7
FIG. 8

BONE FIXATION DEVICE AND METHOD

CROSS REFERENCE TO RELATED APPLICATIONS

This application claims priority to U.S. Provisional Patent Application No. 62/270,229, "BONE FIXATION DEVICE AND METHOD," filed Dec. 21, 2015, which is hereby incorporated by reference in its entirety.

BACKGROUND

Stable fixation of two bone segments having oblique contact surfaces can be difficult. For example, various bones such as clavicles, arm bones such as the humerus, radius and ulna and leg bones such as the femur, tibia and fibula and other similar slanted or askew bones that can be more easily fractured, can utilize a bone fixation device to properly heal. Some injuries can result in angled fractures. For example, the external rotation injuries of the ankle may often result in a short oblique fracture of the lateral malleolus. Because of the oblique orientation of the fracture line, simple apposition of the bone surfaces is nearly always unstable, since axial loading forces on the bone cause sliding of the two bone surfaces along the oblique fracture line and contributes to potential problems of shortening, loss of reduction and non-union or mal-union.

Additionally other long bone fractures can result in pain, loss of function and motion, and eventually arthritis if not healed in the proper length and position. For example in the clavicle, malunion can result in a cosmetic deformity, and functional deformity in the entire arm and shoulder girdle. Similarly, in the forearm a fracture of the radius or ulna or both bones, if allowed to heal in a non-anatomic position, can and usually will result in marked limitation of forearm rotation, and wrist dysfunction.

These types of fractures can lead to future health problems. For fractures involving the lateral malleolus of the ankle, even as little as 1 millimeter of shortening can lead to debilitating arthritis and ankle instability. What are needed both an improved bone fixation device and a method for the stabilization of bone segments having oblique contact surfaces.

SUMMARY OF THE INVENTION

An embodiment of a bone fixation device includes an elongated bone fixation plate and a rotational member. The bone fixation plate can include a plurality of slots and holes for bone screws that are used to secure the fixation plate to an oblique angle fractured bone. The fixation plate can be attached to the bone so that opposite sides of the bone fracture are secured. The bone screws can be placed through the slots in the fixation plate and loosely screwed into the bone segments. Once the bone has been properly aligned, bone screws can be tightened within the slots and additional bone screws can be placed through screw holes in the fixation plate and tightened to securely hold the bone segments in alignment.

The rotation member can be attached to the fixation plate to further support the bone segments. In an embodiment, the rotational member includes two tabs that extend around opposite sides of the bone and fixation plate. The tabs can be perpendicular to the plane of the fixation plate and the center portion of the rotational member. The rotation member can be secured to the fixation plate with a fastener such as a threaded screw and rotated so that the tabs physically contact and prevent movement of the bone segments. In an embodiment, a torque can be applied to the rotational member before the rotational member is rigidly secured to the fixation plate. The contact interface between the fixation plate and the rotational member can have surface features that can prevent rotation of the rotational member after these components are rigidly secured to each other.

BRIEF DESCRIPTION OF THE DRAWINGS

FIG. 3 illustrates a top view of an embodiment of a fixation plate mounted on unaligned fractured bone segments.

FIG. 4 illustrates a top view of an embodiment of a fixation plate initially mounted on aligned fractured bone segments.

FIG. 5 illustrates a top view of an embodiment of a rotational member.

FIG. 6 illustrates an exploded view of an embodiment of a rotational member and fixation plate assembly.

FIG. 7 illustrates an assembled side view of an embodiment of a rotational member and fixation plate assembly before a torque has been applied to the rotational member.

FIG. 8 illustrates an assembled side view of an embodiment of a rotational member and fixation plate assembly after a torque has been applied to the rotational member.

DETAILED DESCRIPTION

Figure 1:
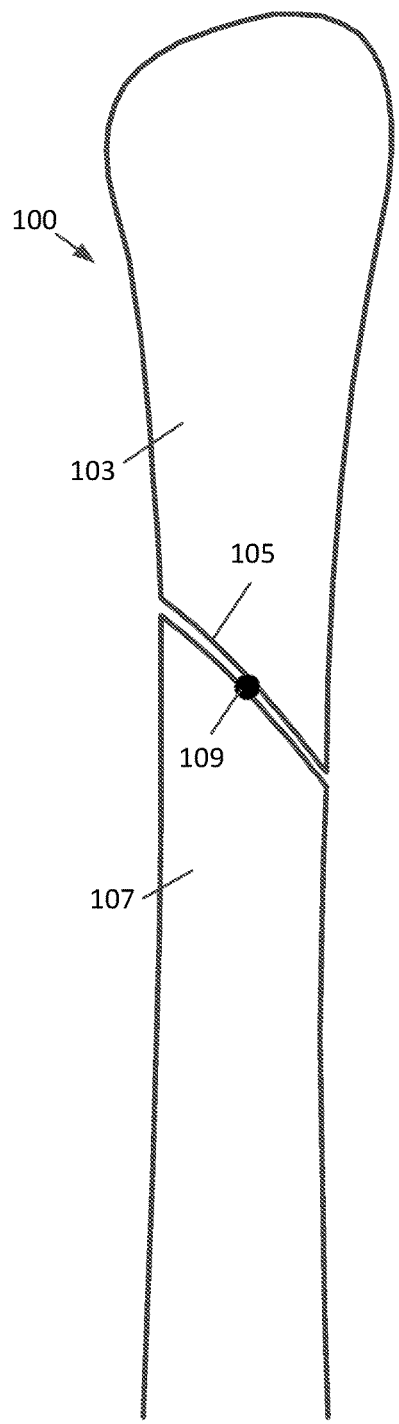
FIG. 1 illustrates a top view of a fractured bone.

The present invention is directed towards an improved bone fixation device and method for stabilization of bone segments having oblique contact surfaces. In the case of an oblique fracture of the lateral malleolus, the opposing bone ends of segments or fragments have the tendency to slide in opposite directions and shorten since axial loading of the bone produces shear stresses contributed by the oblique angle of the fracture surface. With reference to FIG. 1, a bone 100 can be fractured with a first portion 103 and a second portion 107 on opposite sides of a fracture 105. A reference point 109 can be located at the center of the fracture 105. Since the fracture 105 is at an angle, the axial compressive forces on the bone segments 103, 107 causes those segments 103, 107 to slide along the oblique fracture in opposite directions which in turn causes the axial forces on either side of the fracture 105 to askew off center causing bone 100 instability and shortening of the bone.

Figure 2:
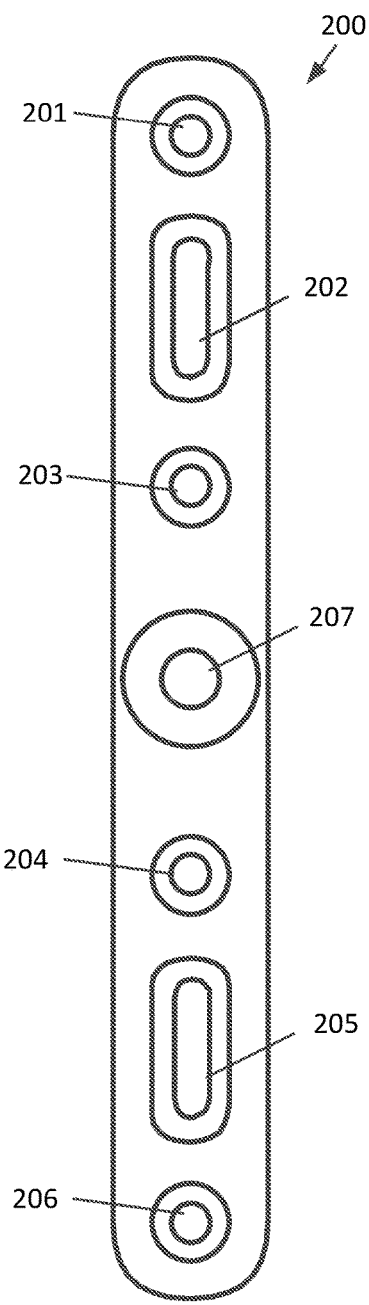
FIG. 2 illustrates a top view of an embodiment of a fixation plate.

With reference to FIG. 2, a top view of an embodiment of a bone fixation plate 200 is illustrated as an elongated structure with a plurality of holes and slots. The cross section of the bone fixation plate 200 can be curved across the width with the lower surface having a concave curvature surface which can be similar in shape to the outer curved surface of the bone shown in FIG. 1. The lower surface of the fixation plate 200 can have an outer concave curvature across the width. The upper surface of the fixation plate 200 can be convex or flat across the width of the fixation plate 200. Bone screws can be used to secure the fixation plate 200 to the bone segments. The holes can include through-holes 201, 203, 204, 206 and slots 202, 205 that extend through the thickness of the fixation plate 200. The holes and slots have contact surfaces that surround the through-holes and slots. The contact surfaces can be planar or conically symmetric surfaces that are axially aligned with the through-holes or slots. The shape of the contact surfaces can correspond to the inner surfaces of the bone screw heads.

With reference to FIG. 3, the fixation plate 200 can be secured to the bone segments 103, 107 by placing threaded bone screws 209 through slots 202, 205. The bone screws 209 can the screwed into the bone segments 103, 107 but may not be tightened. There can be a large gap 301 between the bone segments 103, 107 that may need to be reduced. A rotational member mounting hole 207 can be positioned on a center portion of the fixation plate. In an embodiment, the rotational member mounting hole 207 can have internal threads or any other suitable coupling mechanism.

With reference to FIG. 4, the bone screws 209 can slide within the slots 202, 205. A force can be applied to the bone screws 209 to move the bone segments 103, 107 together and reduce the gap 301. In an embodiment, a special tool can be coupled to the heads of the bone screws 209 to apply a compressive force.

With reference to FIG. 5, a top view of an embodiment of the rotational member 111 is illustrated which can include a body 303 having a center hole 305, a first tab 307 and a second tab 309 extending outwardly and bending in a direction away from the plane of the body 303. The body 303 can have a mechanism for applying a torque force to the rotational member 111. In the illustrated embodiment, the body 303 can have tool holes 311 which can engage a torque tool such as a wrench with torque pins which fit within the tool holes 311.

With reference to FIG. 6, a side exploded view of the rotational member 111, fixation plate 200, bone screw 209 and a cross section of a bone 100 are illustrated. The lower surface of the fixation plate 200 can be a concave surface, which can match the convex outer curvature of the bone 100. The upper surface of the fixation plate 200 can have a planar surface at the contact surface adjacent to the lower center surface the rotational member 111 and a concave surface adjacent to the bone 100. The upper surface of the fixation plate 200 can be parallel to a center axis of the bone 100. In an embodiment, the first tab 307 and the second tab 309 of the rotational member 111 can be parallel and extend in a direction that is perpendicular to a plane of the body 303.

With reference to FIG. 7, the bone screw 209 can be placed through the center hole 305 in the body 303 of the rotational member 111 and a center hole in the fixation plate 200. In an embodiment, the bone screw 209 can be threaded and screwed into the bone 100 to hold the rotational member 111 to the fixation plate 200 and bone 100. In an embodiment, the bone screw 209 may not be fully tightened so that the rotational member 111 can rotate about the bone screw 209.

With reference to FIG. 8, a torque force can be applied to the rotational member 111 and the rotational member 111 can be rotated so that the first tab 307 and the second tab 309 contact and compress opposite sides of the bone 100. The bone 100 can be divided by an oblique fracture with a first portion of the bone and a second portion of the bone on opposite sides of the oblique fracture. The first tab 307 can contact a proximal end of a first portion of the bone 100 and the second tab 309 can contact a distal end of a second portion of the bone 100. When the proper rotational forces or torque is applied to the rotational member 111, the bone screw 209 can be tightened to secure the rotational member 111 in place against the fixation plate 200 and bone 100 to prevent further rotation of the rotational member 111. The rotational member 111 can be in a fixed position relative to the fixation plate 200. When the bone 100 is compressed, the opposite bone sections can slide along the oblique fracture. The first tab 307 and the second tab 309 can be parallel to the plane of the fracture and function to prevent the sliding of the bone 100 along the oblique fracture.

Figures 9, 10:
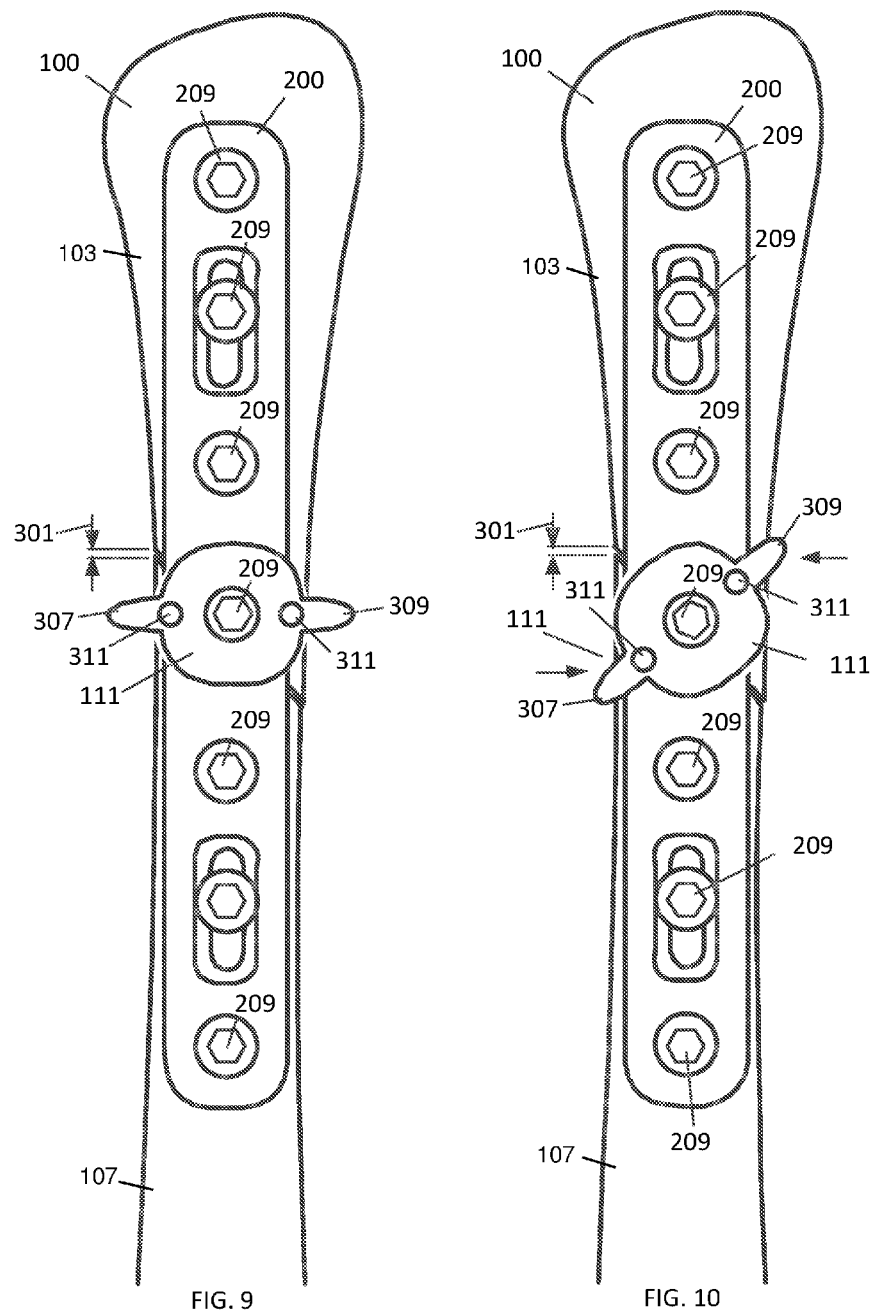
FIG. 9 illustrates an assembled top view of an embodiment of a rotational member and fixation plate assembly before a torque has been applied to the rotational member.
FIG. 10 illustrates an assembled top view of an embodiment of a rotational member and fixation plate assembly after a torque has been applied to the rotational member.

With reference to FIG. 9, a top view of an embodiment of the rotational member 111 on the fixation plate 200 attached to the bone 100 with bone screws 209 is illustrated. Once the bone screws 209 tighten through slots 202, 205 and the rotational member 111 is secured to the fixation plate 200 with a bone screw 209, additional bone screws 209 can be secured to the bone 100 through the holes 201, 203, 204, 206 to rigidly secure the fixation plate 200 to the bone segments 103, 107. With reference to FIG. 10, the rotational member 111 can be rotated to the desired position on the fixation plate 200 and the bone screw 209 can be tightened to hold the rotation member 111 in this position. While the rotational member 111 is shown as being mounted on an outer side of the fixation plate 200 and the bone 100 is shown on the inner side of the fixation plate, in other embodiments, the rotational member 111 can be positioned between the fixation plate 200 and the bone 100.

The fracture between the bone segments 103, 107, can define a fracture plane. The fixation plate 200 can be mounted to the bone 100 so that the fixation plate 200 is perpendicular to the fracture plane 200. When the bone 100 is compressed, the bone segments 103, 107 will tend to slide along the fracture plane. The tabs 307, 309 can be parallel to the fracture plane and are positioned to resist the bone segments 103, 107 from sliding along the fracture plane when the bone 100 is compressed. In this example, the tab 309 contacts the bone segment 103 and applies a force that prevents the bone segment 103 from moving down along the fracture plane while tab 307 is positioned against the bone segment 107 to prevent the bone segment 107 from moving up along the fracture plane.

Figure 11:
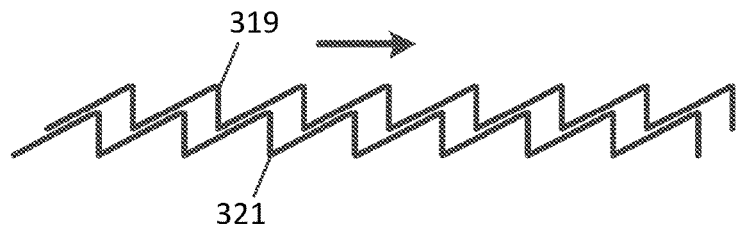
FIG. 11 illustrates an embodiment of an interface of a fixation plate and rotational member with ramped surfaces.
Figure 12:
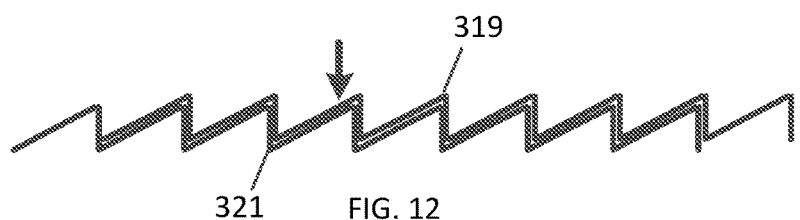
FIG. 12 illustrates an embodiment of an interface of a fixation plate and rotational member with ramped surfaces rigidly secured together.

In an embodiment, the interface between an upper surface of the fixation plate and a lower surface of the rotational member 111 can have surface features that can prevent rotation once the bone screw is tightened. With reference to FIGS. 11 and 12, an embodiment of the contact interface of the fixation plate 321 and the rotational member surfaces 319 are illustrated. In this example, the interface includes a lower surface of the rotational member 319 and an upper surface of the fixation plate 321. The lower surface of the rotational member 319 and the upper surface of the fixation plate 321 are angled so that rotation can be allowed in one direction as designed by the arrow but rotation can also be resisted in the opposite direction. In FIG. 11, the lower surface of the rotational member 319 can be rotated to the desired rotational position relative to the upper surface of the fixation plate 321. With reference to FIG. 12, at the desired rotational position, the bone screw can be tightened to compress the lower surface of the rotational member 319 tightly against the upper surface of the fixation plate 321 to prevent rotation of the rotational member.

Figure 13:
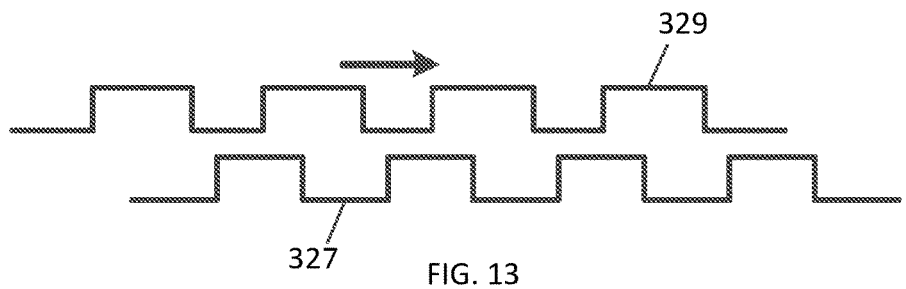
FIG. 13 illustrates an embodiment of an interface of a fixation plate and rotational member with notched surfaces.
Figure 14:
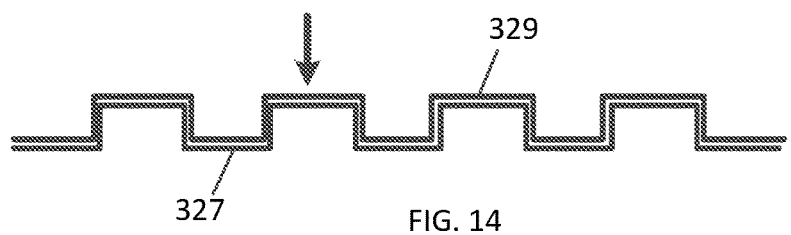
FIG. 14 illustrates an embodiment of an interface of a fixation plate and rotational member with notched surfaces rigidly secured together.
Figure 15:
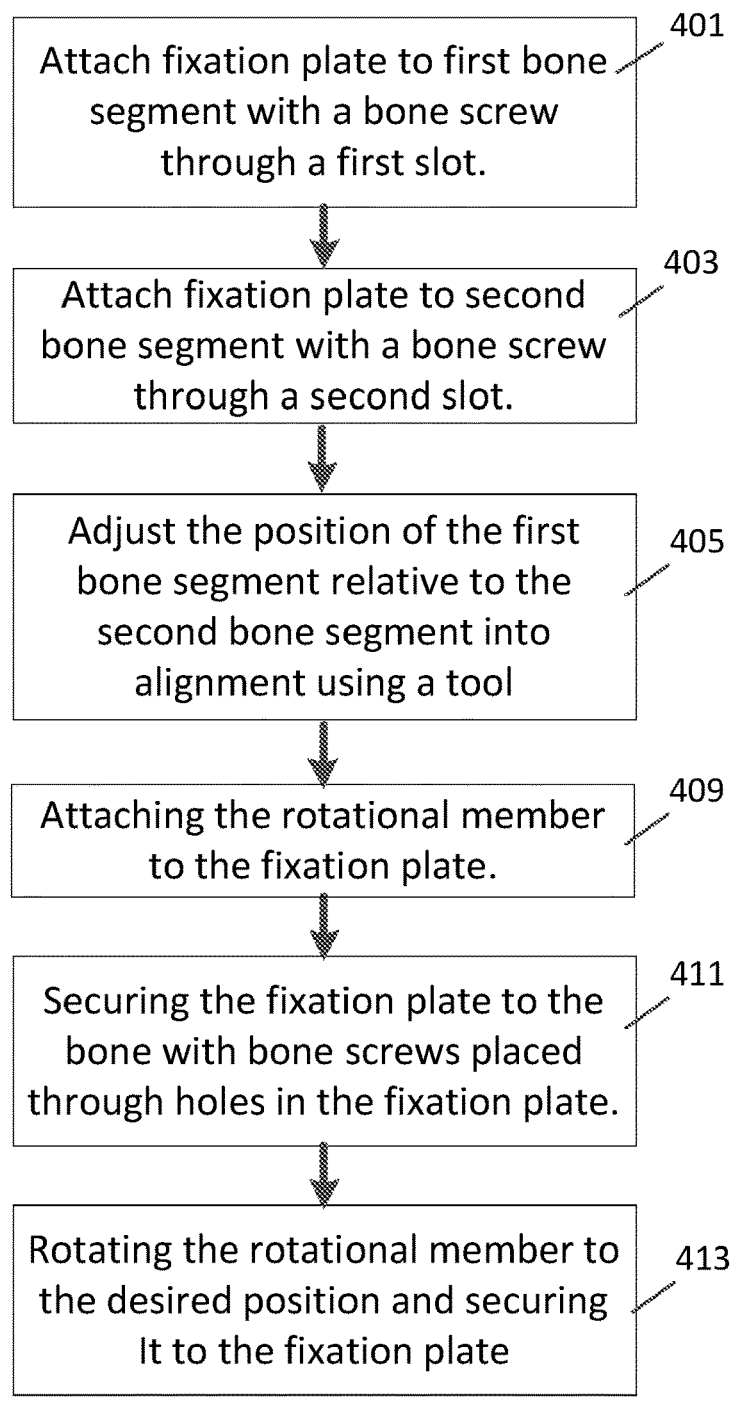
FIG. 15 illustrates an embodiment of a first flowchart for securing a fixation plate and rotational member to a fractured bone.
Figure 16:
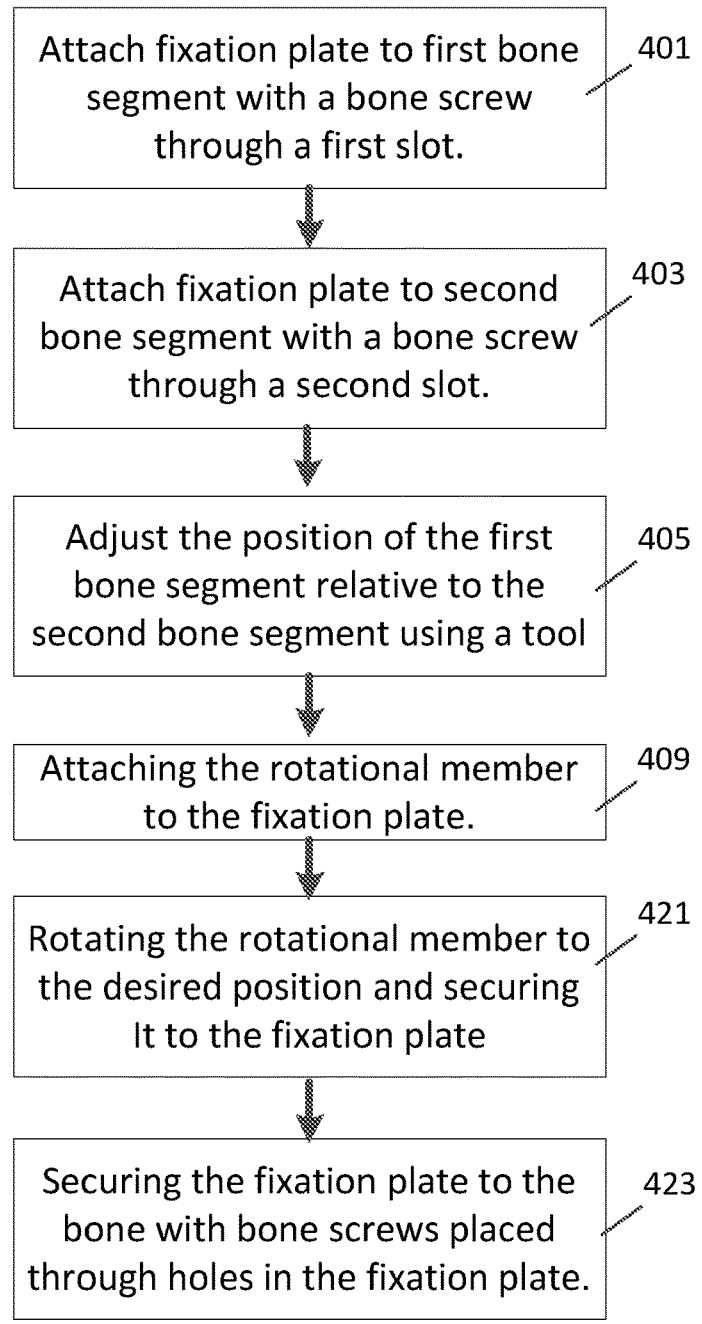
FIG. 16 illustrates an embodiment of a second flowchart for securing a fixation plate and rotational member to a fractured bone.

With reference to FIGS. 13 and 14, another embodiment of a toothed surface interface between a lower surface of the rotational member 329 and an upper surface of the fixation plate 327 is illustrated. In FIG. 13, the lower surface of the rotational member 329 can be separated from the upper surface of the fixation plate 327 so the rotational member can be rotated to the desired position relative to the fixation plate. In FIG. 14, when the rotation member is positioned in the desired rotational position, the bone screw can be tightened to compress the lower surface of the rotational member 329 tightly against the upper surface of the fixation plate 327 so that the teeth interlock to prevent rotation of the rotational member relative to the fixation plate. The illustrated locking mechanisms for securing the fixation plate to the rotational member and to the bone 100 can be based entirely on the bone screws. The holding power of the bone screws is proportional to the purchase of the screw threads in the thin cortex of the bone. FIGS. 15 and 16 illustrate different sequences of steps for securing the fixation plate and rotational member to a fractured bone. While these figures show a specific sequence of steps, in other embodiments, these steps can be performed in any functional order.

The described bone fixation device can be attached as part of a surgical procedure that includes a sequence of process steps. A first example of a surgical procedure is illustrated with reference to FIG. 14. As illustrated in the diagram, the first step is to attach the fixation plate to the first bone segment with bone screw moving through the first slot in the fixation plate 401. The fixation plate 401 is then attached to a second bone segment 403, which is on an opposite side of the bone fracture moving through a second slot with a second bone screw 403. The slots in the fixation plate allow the first and second bone segments to be adjusted and aligned using a tool 405. The fixation plate is then secured to the bone with additional bone screws 411. Next, the rotational member is rotated to the desired rotational position and secured to the fixation plate with a screw to prevent rotation of the rotational plate 413.

Another example of a surgical procedure is illustrated in FIG. 16. The majority of steps in this alternative surgical procedure are the same as FIG. 15. After the rotational member is attached to the fixation plate 409, the rotational member is rotated to the desired position and secured to the fixation plate with a bone screw 421. The fixation plate can then be secured to the bone with additional bone screws placed through mounting holes in the fixation plate 423.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. As a person skilled in the art will recognize from the previous detailed description and from the figures, modifications and changes can be made to the preferred embodiments of the invention without departing from the scope of this invention.

What is claimed is:

1. An apparatus for fixation of a fractured bone, comprising:

an elongated fixation plate having a longitudinal axis adapted to extend along a long axis of the fractured bone and including a first portion extending along the longitudinal axis of the fixation plate adapted for attachment to a first fragment of the fractured bone and a second portion extending in an opposite direction from the first portion along the longitudinal axis of the plate adapted for attachment to a second fragment of the fractured bone such that the fixation plate is adapted to extend across a fracture between the first fragment and the second fragment of the fractured bone;

a rotational member having a body and a first tab and a second tab extending outwardly and bending in a direction away from a plane of the body; and a fastener for attaching the body of the rotation member to the elongated fixation plate;

wherein the tabs extending outwardly from the body are adapted for engaging the fractured bone to apply force to the first and second fragments transversely across opposite sides of the fractured bone to produce a torque across the fracture.

2. The apparatus of claim 1 further comprising:
a rotational resistance mechanism between the body of the rotational member and the elongated fixation plate.

3. The apparatus of claim 2 wherein the rotational resistance mechanism prevents rotation of the rotational member relative to the elongated fixation plate.

4. The apparatus of claim 2 wherein the rotational resistance mechanism includes a first plurality of teeth on a lower surface of the body of the rotational member and a second plurality of teeth on an upper surface of the fixation plate and wherein the first plurality of teeth and the second plurality of teeth are held against each other by the fastener.

5. The apparatus of claim 2 wherein the fastener is a component of the rotational resistance mechanism, the rotational resistance mechanism allows rotation of the rotational member when the fastener is loosened and the rotational resistance mechanism prevents rotation of the rotational member when the fastener is tightened.

6. The apparatus of claim 1, wherein the tabs of the rotational member are positioned for engaging respective surfaces of the fragments, on opposite sides of the fracture.

7. The apparatus of claim 1, wherein the elongated fixation plate includes one or more slots.

8. The apparatus of claim 1, wherein the body of the rotational member includes a torque coupling for engaging a torque tool.

9. The apparatus of claim 8, wherein the torque coupling includes a recess or a protrusion with geometric features which releasably engage a driver with corresponding geometric features of the torque tool.

10. A method for securing a fixation plate to a fractured bone, comprising:

providing an elongated fixation plate having a plurality of fixation holes, a first fastener point and a concave inner surface, a rotational member having a body with a second fastener point and a first tab and a second tab extending outwardly from the body and bending in a direction away from a plane of the body and a fastener for attaching the first fastener point of the fixation plate to the second fastener point of the body of the rotation member;

attaching the elongated fixation plate along a long axis of the fractured bone wherein a first portion of the elongated fixation plate is attached to a first fragment of the fractured bone and a second portion of the elongated fixation plate is attached to a second fragment of the fractured bone such that the fixation plate extends across a fracture of the fracture bone; and coupling the rotational member to the elongated fixation plate so that the first tab and the second tab of the rotational member are positioned against opposite sides of the fractured bone.

11. The method of claim 10 further comprising:

applying a first torque to the body of the rotational member so that the first tab and the second tab apply compressive forces to the fractured bone.

12. The method of claim 11 wherein the first torque applied to the body of the rotational member is between 0.1 foot pound and 10 foot pound.

13. The method of claim 11 further comprising:

coupling a torque tool having an elongated handle to the rotational member; and rotating the torque tool to apply the first torque to the body.

14. The method of claim 10 further comprising:

actuating a rotational resistance mechanism to prevent rotation of the rotational member relative to the fixation plate while a rotational torque is being applied to the body of the rotational member.

15. The method of claim 14 wherein the rotational resistance mechanism includes a threaded screw that is tightened to actuate the rotational resistance mechanism to prevent rotation of the rotational member relative to the fixation plate.

16. The method of claim 14 further comprising:

deactuating the rotational resistance mechanism to allow rotation of the rotational member relative to the fixation plate;

applying a first torque to the body of the rotational member so that the first tab and the second tab apply compressive forces to the fractured bone; and reactuating the rotational resistance mechanism to prevent rotation of the rotational member relative to the fixation plate.

17. The method of claim 10 further comprising:

adjusting a position of the first bone fragment while the first bone fragment and the second bone fragment are in physical contact with the elongated fixation plate to change the fracture between the first bone fragment and the second bone fragment.

18. The method of claim 10 wherein the tabs extending outwardly from the body are adapted for engaging the fractured bone to apply force to the first and second fragments transversely across opposite sides of the fractured bone to produce a torque across the fracture.

* * * * *